United States Patent [19]

Ronsen et al.

[11] Patent Number: 5,672,612
[45] Date of Patent: Sep. 30, 1997

[54] AMORPHOUS PAROXETINE COMPOSITION

[75] Inventors: Bruce Ronsen, River Forest; Ragab El-Rashidy, Deerfield, both of Ill.

[73] Assignee: Pentech Pharmaceuticals, Inc., Wheeling, Ill.

[21] Appl. No.: 708,802

[22] Filed: Sep. 9, 1996

[51] Int. Cl.⁶ ............................................. A61K 31/44
[52] U.S. Cl. ............................................. 514/338; 546/197
[58] Field of Search ............................ 514/338; 546/197

[56] References Cited

U.S. PATENT DOCUMENTS

| | | | |
|---|---|---|---|
| 4,007,196 | 2/1977 | Chistensen et al. | 260/293.58 |
| 4,721,723 | 1/1988 | Barnes et al. | 514/321 |
| 5,151,448 | 9/1992 | Crenshaw et al. | 514/651 |
| 5,276,042 | 1/1994 | Crenshaw et al. | 514/321 |

*Primary Examiner*—Amelia Owens
*Attorney, Agent, or Firm*—Olson & Hierl, Ltd.

[57] ABSTRACT

A free-flowing, amorphous paroxetine hydrochloride-ethanol composition suitable as a therapeutic agent for premature ejaculation can be prepared by dissolving paroxetine free base in a hydrochloric acid-ethanol solution followed by drying. In a preferred embodiment, the amount of ethanol present in the amorphous product is in the range of 1 to 4 weight percent based on paroxetine hydrochloride. The amorphous product is stable and substantially non-hygroscopic.

11 Claims, 4 Drawing Sheets

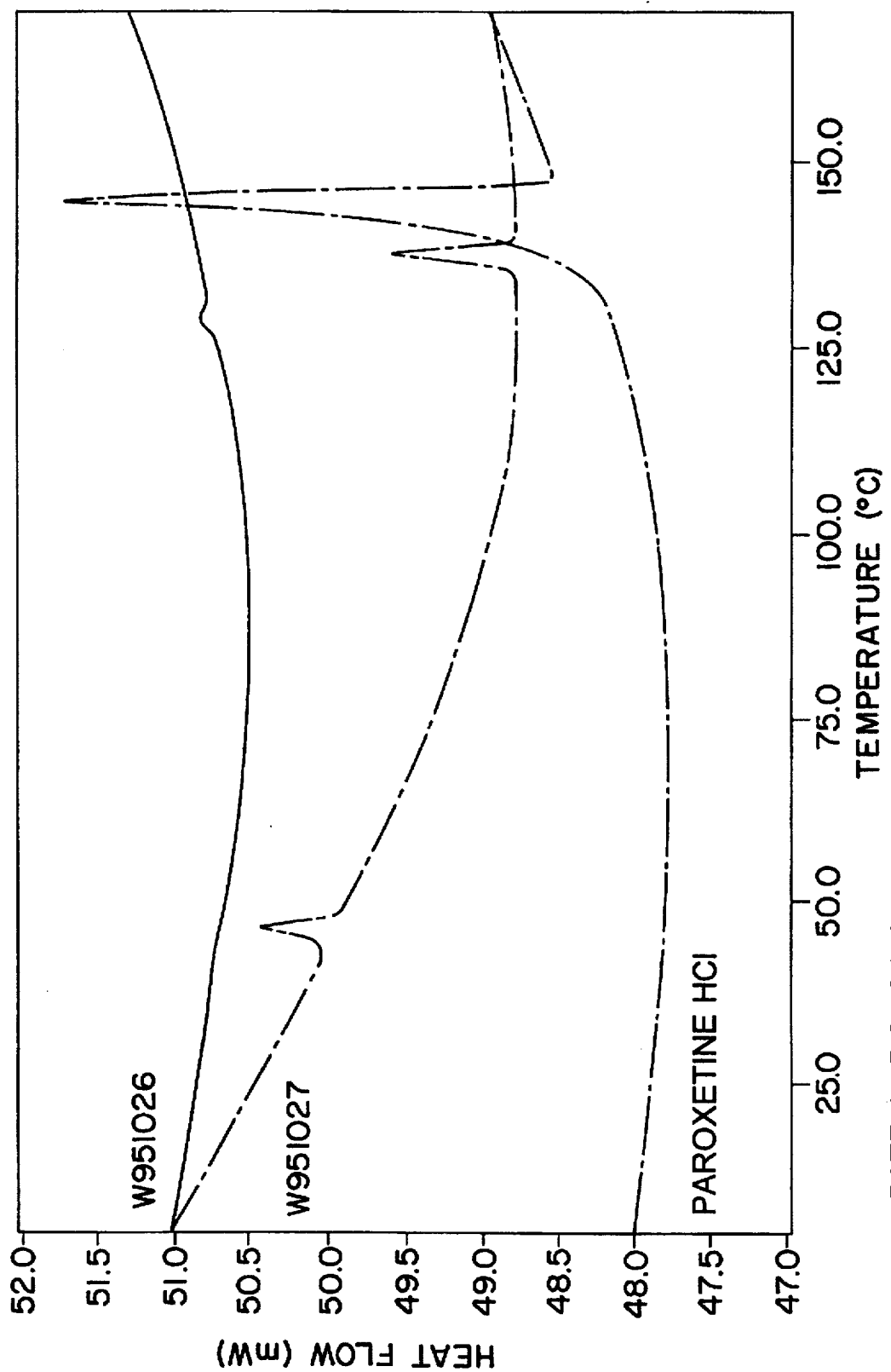

AMORPHOUS PAROXETINE COMPOSITION

FIELD OF THE INVENTION

This invention relates to an amorphous paroxetine composition suitable as a therapeutic agent for sexual dysfunction and to a process for preparing such composition.

BACKGROUND OF THE INVENTION

The selective serotonin reuptake inhibitor (SSRI) antidepressants have recently emerged as effective new treatments for patients with premature ejaculation. In general, antidepressants influence more than one neurotransmitter system and have affinity for multiple receptors. This heterogeneity of action produces mixed effects, including those on the sexual response cycle. Sexual dysfunction associated with antidepressants, including delayed and completely abolished ejaculation, has been a subject of numerous case reports, studies, and review articles [for example, J. Clin. Psychiatry 54, 209–212, (1993); J. Clin. Psychopharmacol. 3, 76–79, (1983); J. Clin. Psychiatry Mon. 10, 4–10, (1992); Depression 2, 233–240, (1994/1995)]. Because of the lack of abuse potential, relatively benign side effect profile, and fairly consistent reports of delayed ejaculation, SSRI antidepressants seem to be a safe treatment option for patients with premature ejaculation, especially in cases of failed psychological treatment.

The use of the SSRI antidepressant fluoxetine hydrochloride (Prozac®) in this regard has been described in U.S. Pat. No. 5,151,448 to Crenshaw et al. A similar treatment, at a relatively lower dosage of active ingredient, has been described in U.S. Pat. No. 5,276,042 to Crenshaw et al. for the SSRI antidepressant paroxetine hydrochloride (Paxil®). Other anti-anxiety drugs such as chlordiazepoxide (Librium®) and diazepam (Valium®) are not suitable for the treatment of premature ejaculation.

The preparation of a class of SSRI antidepressants has been disclosed in U.S. Pat. No. 4,007,196 to Christensen et al. In Example 2 of this patent, the preparation of (−)-trans-4R-(4'-fluorophenyl)-3S-[(3'4'-methylenedioxy-phenoxy) methyl]-piperidine (generic name paroxetine) is described (formula A),

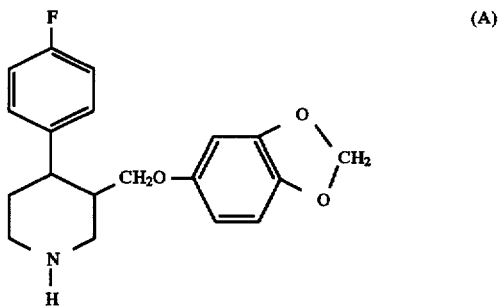

(A)

wherein paroxetine is obtained as a free base then converted to its maleic acid salt. The use of the acetate salt of paroxetine has been described [Psychopharmacology 57, 151–153 (1978); Psychopharmacology 68, 229–233 (1980); European Journal of Pharmacology 47, 351–358 (1978)]. There also has been limited use of the hydrochloride salt in aqueous solution [Acta. Pharmacol. et Toxicol. 44, 289–295 (1979)]. More recently, U.S. Pat. No. 4,721,723 to Barnes et al. has disclosed the preparation of a crystalline paroxetine hydrochloride hemihydrate. However, this particular process requires post-synthetic treatment of the product in order to obtain the crystalline adds to the difficulty and overall cost of production. Amorphous paroxetine hydrochloride has been reported by Barnes et al. to be undesirably hygroscopic.

The present invention provides an economical manufacturing process for the preparation of a substantially non-hygroscopic, free-flowing, amorphous paroxetine hydrochloride-ethanol composition suitable as a therapeutic agent for the treatment of premature ejaculation.

SUMMARY OF THE INVENTION

Amorphous paroxetine hydrochloride-ethanol composition and method for its production are disclosed. The present inventive method generates amorphous, substantially non-hygroscopic paroxetine hydrochloride from a reaction of paroxetine base with a hydrochloric acid/ethanol solution followed by drying of the product. This invention overcomes inherent problems associated with crystallization methods of the prior art, including the recovery of product.

The paroxetine base can be prepared according to the procedure set forth in U.S. Pat. No. 4,007,196 to Christensen et al. Paroxetine hydrochloride solute is obtained by combining an appropriate amount of hydrochloric acid in absolute ethanol with the free base. The amorphous composition is produced upon drying of the product. In a preferred embodiment, the amount of ethanol present in the product is not more than about 10 percent by weight based on the paroxetine hydrochloride. Under this condition, the amorphous composition is a substantially non-hygroscopic solid, thus providing a manufacturing advantage. In a more preferred embodiment, the amount of ethanol present in the composition is in the range of about 1 to about 4 weight percent, based on paroxetine hydrochloride. This amorphous composition is stable and is amenable to incorporation into both tablet and suppository dosage forms.

BRIEF DESCRIPTION OF THE DRAWINGS

In the drawings,

FIG. 3A illustrates the results of differential scanning calorimetry done at a heating rate of 5° C./minute on the reference sample paroxetine hydrochloride and two amorphous samples, lot #'s W951027 and W951026. The horizontal axis represents temperature (°C.) and the vertical axis corresponds to the heat flow (mW).

DETAILED DESCRIPTION OF PREFERRED EMBODIMENTS

A free-flowing, substantially non-hygroscopic solid form of paroxetine hydrochloride-ethanol is obtained by combining paroxetine base with a hydrochloric acid/ethanol solution and drying of the product. The drying step can be effected by spray-drying, vacuum drying and the like.

The paroxetine base can be obtained according to the procedure of U.S. Pat. No. 4,007,196 to Christensen et al.

Absolute ethanol is added in an amount sufficient to dissolve the paroxetine base, the molar ratio of paroxetine base to absolute ethanol preferably being in the range of about 10% v/v to about 15 % w/v. A solution of hydrochloric acid in absolute ethanol preferably in the range of about 10% v/v to about 30% v/v, usually about 22% v/v, is added to the paroxetine base solution and stirred at ambient temperature and pressure for a time period sufficient to produce paroxetine hydrochloride salt. The preferred molar ratio of paroxetine base to hydrochloric acid is in the range of about 1:1 to about 1:10. The reaction temperature is preferably in the range of about 15° C. to about 40° C. along with a preferred reaction time in the range of about 10 minutes to about 40 minutes. The resulting solution was then dried by rotary evaporation or spray drying to obtain the desired amorphous paroxetine hydrochloride-ethanol composition. The drying time preferably ranges from about 8 hours to about 72 hours. The amount of ethanol present in the final product relative to paroxetine hydrochloride is not more than about 10 weight percent, more preferably in the range of about 1 to about 4 weight percent.

Example 1

Figure 1:
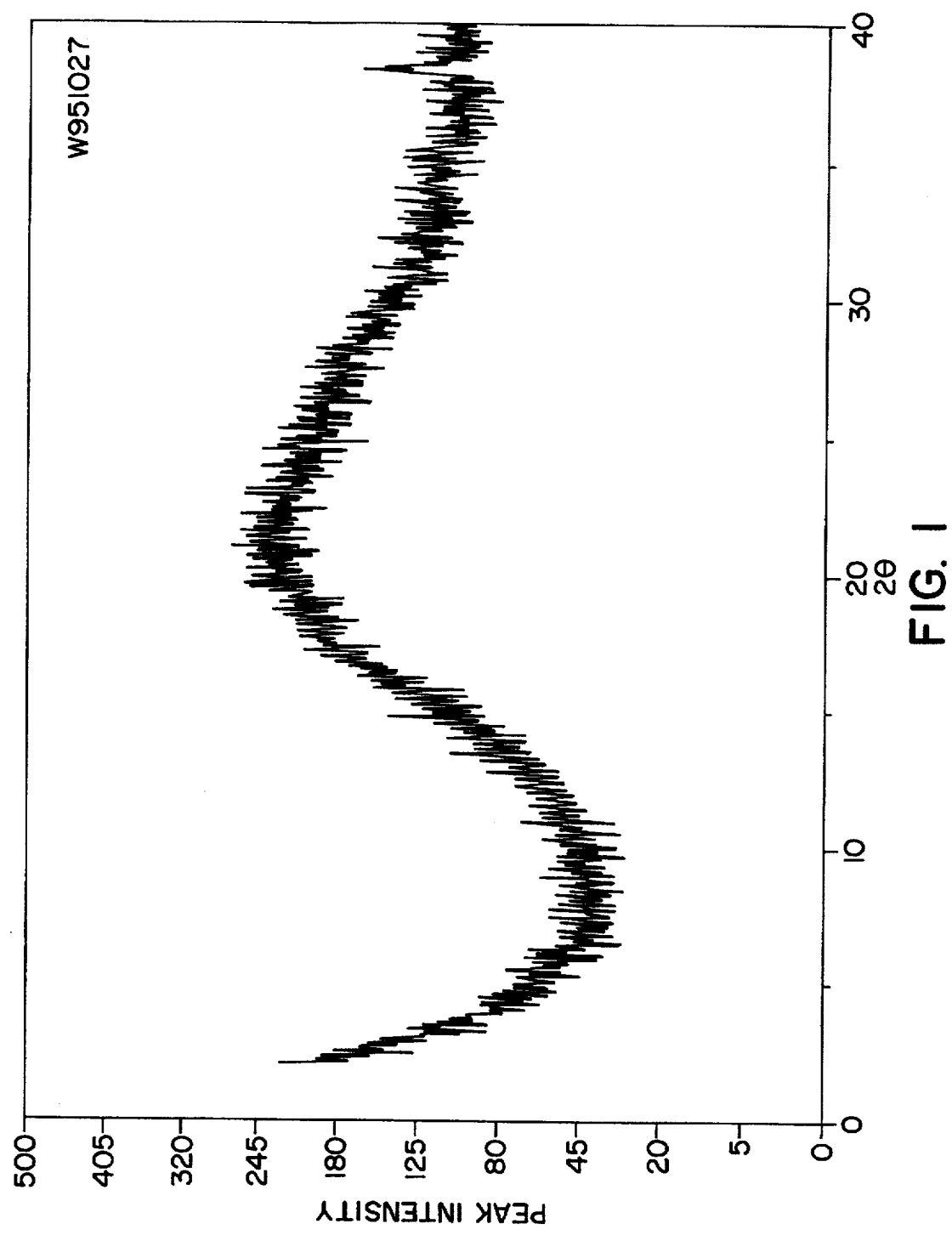
FIG. 1 is the diffraction pattern of the amorphous paroxetine composition, lot #W951027. The horizontal axis represents 2θ and the vertical axis corresponds to peak intensity.
Figure 3B:
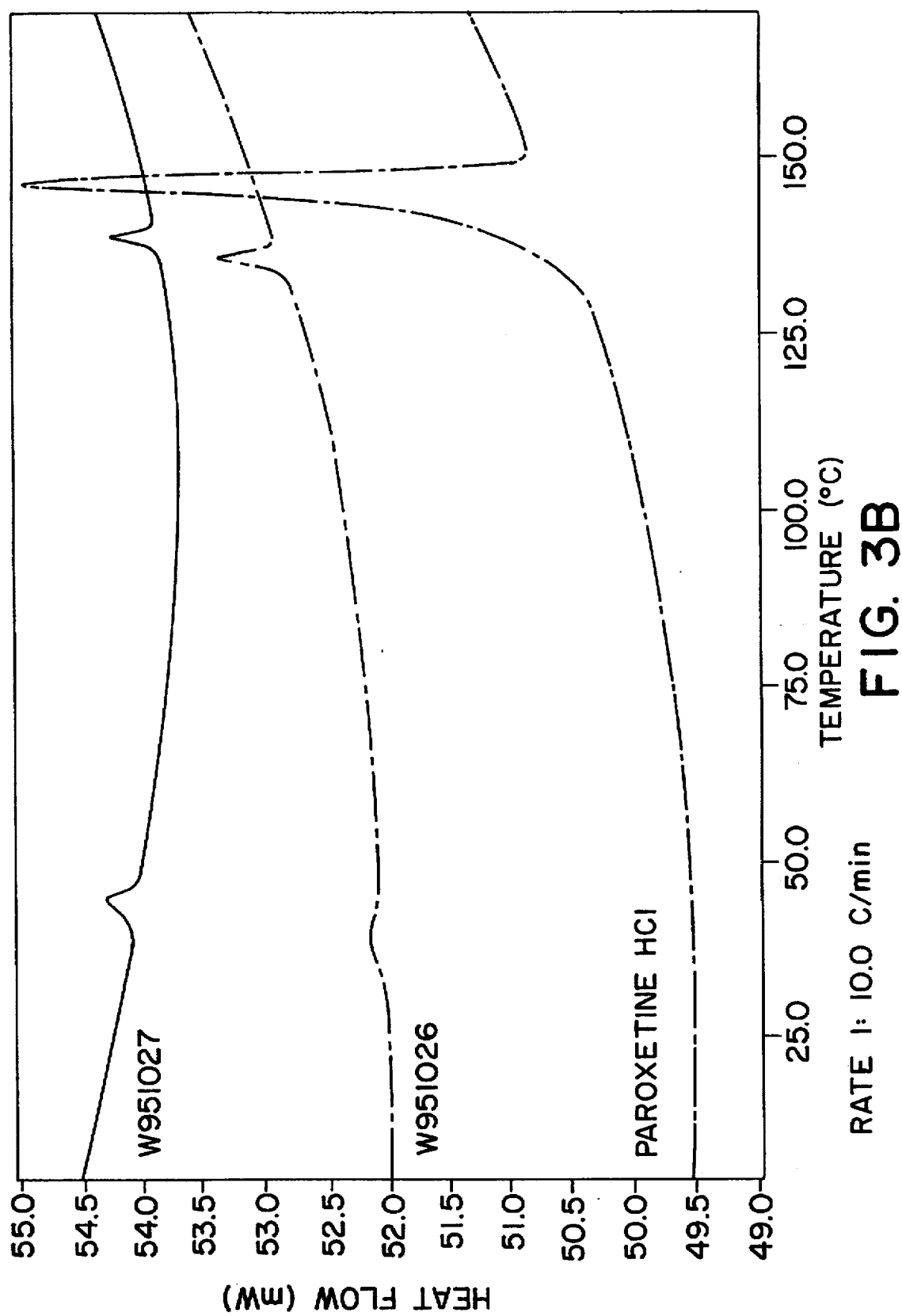
FIG. 3B illustrates the results of differential scanning calorimetry done at a heating rate of 10° C./minute on the reference sample paroxetine hydrochloride and two amorphous samples, lot #'s W951027 and W951026. The horizontal axis represents temperature (°C.) and the vertical axis corresponds to the heat flow (mW).

Preparation of Amorphous Paroxetine HCl-Ethanol Composition: Vacuum Drying Method To a reaction flask containing 100 ml of absolute ethanol was added to 13.9 g of paroxetine base. The flask was shaken until a clear solution was obtained. To this paroxetine solution, 10 ml of a solution of hydrochloric acid in absolute ethanol (22% v/v) was added dropwise. As the reaction proceeded to completion, the color of the solution changed from a yellow brown to a pink brown. The product was then vacuum dried in a rotary evaporator. A foamy, amorphous solid was obtained (lot #W951027). The produced amorphous solid was subjected to an additional 2.5 days of drying in a dessicator at reduced pressure. The solid, a free-flowing powder, was tested for composition by NMR and FTIR. The findings were consistent with published spectra for paroxetine. Silver nitrate testing of the solid indicated the presence of chloride in the sample. Volatile analysis by gas chromatography revealed that the amount of ethanol present in the amorphous solid was 4% by weight. Residual moisture was determined by Karl-Fisher coulometric method at 0.7%. HPLC analysis revealed the material was >99% pure and essentially free from contamination. X-ray powder crystallography was conducted on the sample and produced the diffraction pattern shown in FIG. 1. X-ray powder diffraction was performed using the powder pack method. The powder patterns were obtained using a Philips PW1710 automated diffractometer, with monochromatized $CuK_\alpha$ ($K_{\alpha 1}$=1.54060 Å; $K_{\alpha 2}$=1.54438 Å) radiation. The diffractometer was equipped with a compensating slit and a graphite monochromator. It was calibrated to 0.02° (2θ) using the quartz peak at 26.66° (2θ). The minimum peak/background ratio was 0.75. This spectrum is consistent with an amorphous solid form. The halo effect is clearly seen and the intensity is small. Differential scanning calorimetry was performed on the solid at two different heating rates. The results indicate an endotherm at 48° C. (heat flow) with and absence of other endotherms (FIG. 3A and FIG. 3B). Visual examination showed a "glassing" of the solid at this temperature.

A specimen (0.5 g) was stored in a glass container with a HDPE liner for stability testing. The container was opened and closed periodically exposing the specimen to atmospheric moisture. Moisture determination was conducted at intervals of about 3 months. Appearance of the material was noted, summarized in TABLE 1, below.

TABLE 1

Stability of Paroxetine-HCl/ethanol, amorphous, lot #W951027

| TIME | Initial | 3 months | 6 months |
|---|---|---|---|
| APPEARANCE | Free-flowing powder | Free-flowing powder | Free-flowing powder |
| MOISTURE | 0.7% w/w | 1.8% w/w | 2.1% w/w |

EXAMPLE 2

Figure 2:
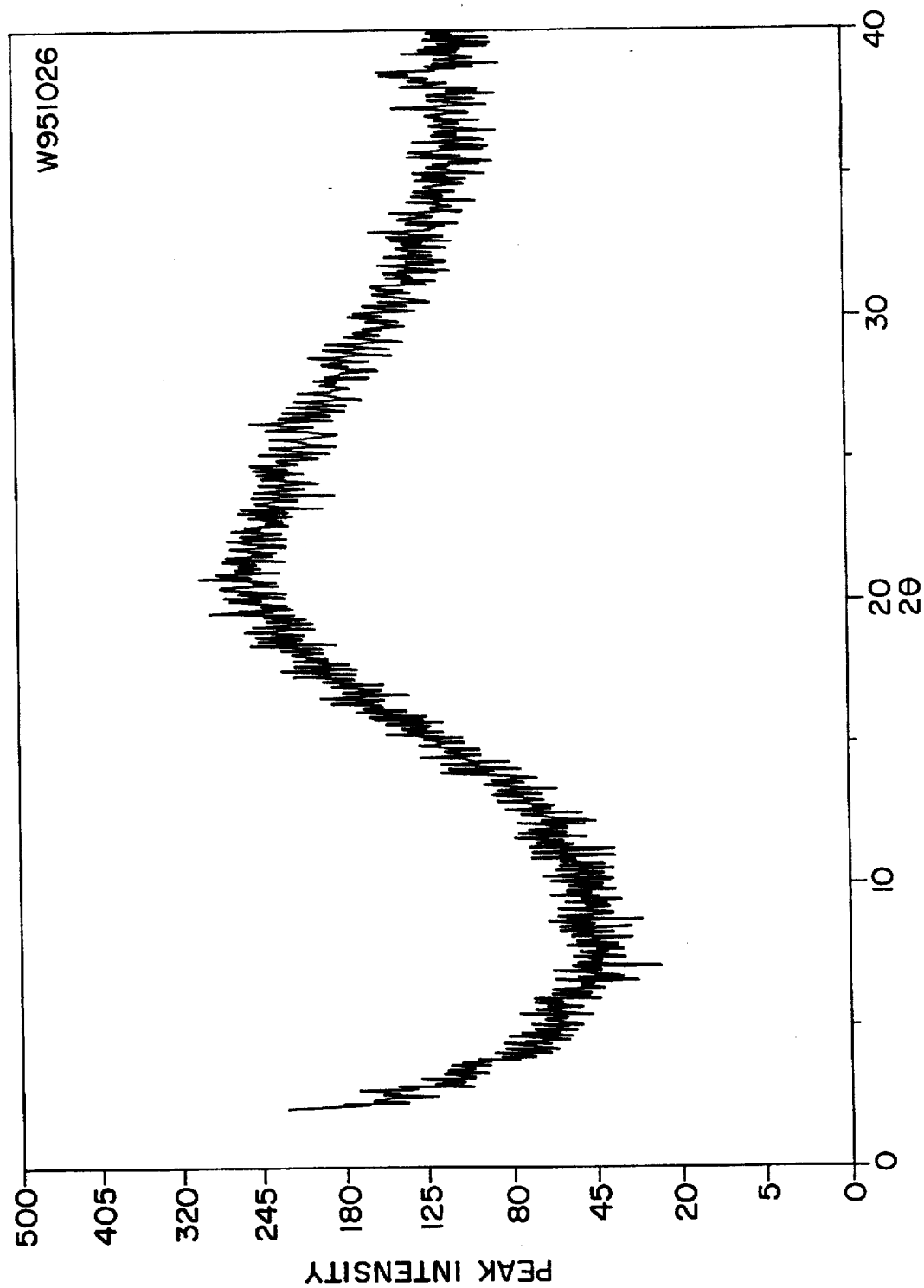
FIG. 2 is the diffraction pattern of the amorphous paroxetine composition, lot g W951026. The horizontal axis represents 2θ and the vertical axis corresponds to peak intensity.

Preparation of Amorphous Paroxetine-HCl/Ethanol Composition: Spray Drying Method A solution of paroxetine hydrochloride in absolute ethanol (3.2 g/100 ml) was prepared as described in EXAMPLE 1. The solution was charged into a spray-drying machine (Yamato Chemical Co.) using a standard nozzle (0.1 mm orifice). The inlet temperature was set at 90° C. and the outlet temperature at 60° C. The sample was spray dried to a fine, off-white powder (lot #W951026). Following recovery, the material was transferred to a vacuum dessicator and dried under partial vacuum for an additional 2.5 days. The resulting solid, a free-flowing powder, was tested for composition by NMR and FTIR. The findings were consistent with published spectra for paroxetine. Silver nitrate solution addition to an aqueous solution of the powder produced a white precipitate indicative of chloride. Volatile analysis by gas chromatography revealed that the amount of ethanol residual was about 0.3% w/w. Residual moisture in the product was 0.8% measured by Karl-Fisher coulometric method. A sample was analyzed by HPLC and found to be free from related substances (purity >99%). X-ray powder crystallography was conducted producing the diffraction pattern shown in FIG. 2. This spectrum is consistent with an amorphous form. Differential scanning calorimetry was conducted on the solid. The results showed an endotherm at 48° C. (see FIG. 3A and FIG. 3B). Visual examination of the sample showed a "glassing" of the solid at this temperature.

For stability testing a specimen (9 g) was stored in a glass container with a HDPE liner. The container was opened and closed periodically exposing the specimen to atmospheric moisture. Moisture determination was conducted at intervals of about 3 months. Appearance of the material was noted with the findings summarized in TABLE 2, below.

TABLE 2

Stability of Paroxetine HCl/ethanol, amorphous, lot #W951026

| TIME | Initial | 3 months | 6 months |
|---|---|---|---|
| APPEARANCE | Free-flowing powder | Free-flowing powder | Free-flowing powder |
| MOISTURE | 0.8% w/w | 2.1% w/w | 2.2% w/w |

The foregoing is intended to be illustrative of the present invention, but not limiting. Numerous variations and modifications of the present invention may be effected without departing from the true spirit and scope of the invention.

We claim:

1. A solid, stabilized amorphous paroxetine hydrochloride composition which comprises paroxetine hydrochloride and ethanol; the ethanol being present in the composition in an amount not more than about 10 percent by weight, based on said paroxetine hydrochloride.

2. The composition in accordance with claim 1 wherein said ethanol is present in an amount in the range of about 1 to about 4 weight percent, based on said paroxetine hydrochloride.

3. The composition in accordance with claim 1 and in tablet form.

4. The composition in accordance with claim 1 and in suppository form.

5. A process for the production of an amorphous paroxetine hydrochloride-ethanol composition comprising:

(a) dissolving paroxetine free base in absolute ethanol;

(b) adding a solution of hydrochloric acid in absolute ethanol to the paroxetine base solution;

(c) stirring the resulting solution for a period of time sufficient to produce a composition of paroxetine hydrochloride in ethanol; and (d) drying the paroxetine hydrochloride-ethanol composition.

6. The method of claim 5 wherein the reaction temperature is in the range of about 15° C. to 40° C.

7. The method of claim 5 wherein the ratio of paroxetine base to absolute ethanol is in the range of about 10% w/v to about 15% w/v.

8. The method of claim 5 wherein the molar ratio of paroxetine base to hydrochloric acid is in the range of about 1:1 to about 1:10.

9. The method of claim 5 wherein the ratio of hydrochloric acid to ethanol is in the range of about 10% v/v to about 30% v/v.

10. The method of claim 5 wherein the reaction time is in the range of about 10 minutes to about 40 minutes.

11. The method of claim 5 wherein the drying time is in the range of about 8 hours to about 72 hours.

* * * * *